(12) United States Patent
De Paul et al.

(10) Patent No.: US 9,067,962 B2
(45) Date of Patent: Jun. 30, 2015

(54) METHODS OF TREATING DIABETES

(75) Inventors: Susan Margaret De Paul, Zürich (CH);
Anett Perlberg, Gunzgen (CH);
Matthew Mangzhu Zhao, Edison, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 322 days.

(21) Appl. No.: 13/530,645

(22) Filed: Jun. 22, 2012

(65) Prior Publication Data

US 2013/0165395 A1    Jun. 27, 2013

Related U.S. Application Data

(63) Continuation of application No. 12/503,225, filed on Jul. 15, 2009, now Pat. No. 8,217,156.

(60) Provisional application No. 61/081,423, filed on Jul. 17, 2008.

(51) Int. Cl.
*C07H 15/14* (2006.01)
*A61K 31/7028* (2006.01)
*A61K 31/7034* (2006.01)
*C07H 7/04* (2006.01)

(52) U.S. Cl.
CPC .................. *C07H 15/14* (2013.01); *C07H 7/04* (2013.01); *A61K 31/7034* (2013.01); *A61K 31/7028* (2013.01)

(58) Field of Classification Search
None
See application file for complete search history.

(56) References Cited

U.S. PATENT DOCUMENTS

| | | | |
|---|---|---|---|
| 7,781,577 B2 * | 8/2010 | Harrison et al. | 536/29.1 |
| 7,846,945 B2 * | 12/2010 | Harrison et al. | 514/317 |
| 8,026,347 B2 | 9/2011 | Goodwin | |
| 8,217,156 B2 | 7/2012 | De Paul | |
| 2006/0035841 A1 | 2/2006 | Eckhardt | |
| 2006/0189548 A1 | 8/2006 | Himmelsbach | |
| 2008/0113922 A1 * | 5/2008 | Harrison et al. | 514/23 |
| 2008/0221164 A1 * | 9/2008 | Goodwin et al. | 514/328 |
| 2010/0311673 A1 | 12/2010 | Harrison et al. | |

OTHER PUBLICATIONS

Handlon, A.L., *Expert Opin Therapeutic Patents* 15(11):1531-1540 (2005).
Search Report and Written Opinion for Corresponding International Application PCT/US2009/050636, dated Jul. 17, 2008.

* cited by examiner

*Primary Examiner* — Eric Olson
(74) *Attorney, Agent, or Firm* — Max Bachrach

(57) ABSTRACT

Solid forms of anhydrous (2S,3R,4R,5S,6R)-2-(4-chloro-3-(4-ethoxybenzyl)phenyl)-6-(methylthio)tetrahydro-2H-pyran-3,4,5-triol are disclosed, in addition to methods of their use in the treatment of various diseases and disorders.

16 Claims, 4 Drawing Sheets

METHODS OF TREATING DIABETES

This is a continuation of U.S. application Ser. No. 12/503,225, filed Jul. 15, 2009, which claims priority to U.S. provisional patent application No. 61/081,423, filed Jul. 17, 2008, the entireties of which are incorporated herein by reference.

1. FIELD OF THE INVENTION

This invention relates to solid forms of (2S,3R,4R,5S,6R)-2-(4-chloro-3-(4-ethoxybenzyl)phenyl)-6-(methylthio)tetrahydro-2H-pyran-3,4,5-triol, and to methods of their use.

2. BACKGROUND OF THE INVENTION

Different solid forms of the same compound can have substantially different properties. For example, the amorphous form of a drug may exhibit different dissolution characteristics and different bioavailability patterns than its crystalline form(s), properties which can affect how the drug must be administered to achieve optimal effect. Amorphous and crystalline forms of a drug may also have different handling properties (e.g., flowability, compressibility), dissolution rates, solubilities and stabilities, all of which can affect the manufacture of dosage forms. Consequently, access to multiple forms of a drug is desirable for a variety of reasons. Moreover, regulatory authorities (e.g., the U.S. Food and Drug Administration) may require the identification of all solid (e.g., polymorphic) forms of a new drug substance before products containing it. A. Goho, *Science News* 166(8): 122-123 (2004).

Compounds may exist in one or more crystalline forms, but the existence and characteristics of those forms cannot be predicted with any certainty. In addition, no standard procedure exists for the preparation of all possible polymorphic forms of a compound. And even after one polymorph has been identified, the existence and characteristics of other forms can only be determined by additional experimentation. Id.

3. SUMMARY OF THE INVENTION

This invention is directed, in part, to amorphous and crystalline solid forms of anhydrous (2S,3R,4R,5S,6R)-2-(4-chloro-3-(4-ethoxybenzyl)phenyl)-6-(methylthio)tetrahydro-2H-pyran-3,4,5-triol, which is an inhibitor of sodium glucose co-transporter 2.

One embodiment of the invention encompasses pharmaceutical compositions comprising the solid forms described herein.

Another embodiment encompasses methods of inhibiting SGLT2 activity, as well as methods of treating, preventing and managing a variety of diseases and disorders, using the solid forms described herein.

4. BRIEF DESCRIPTION OF THE FIGURES

5. DETAILED DESCRIPTION OF THE INVENTION

Figure 1:
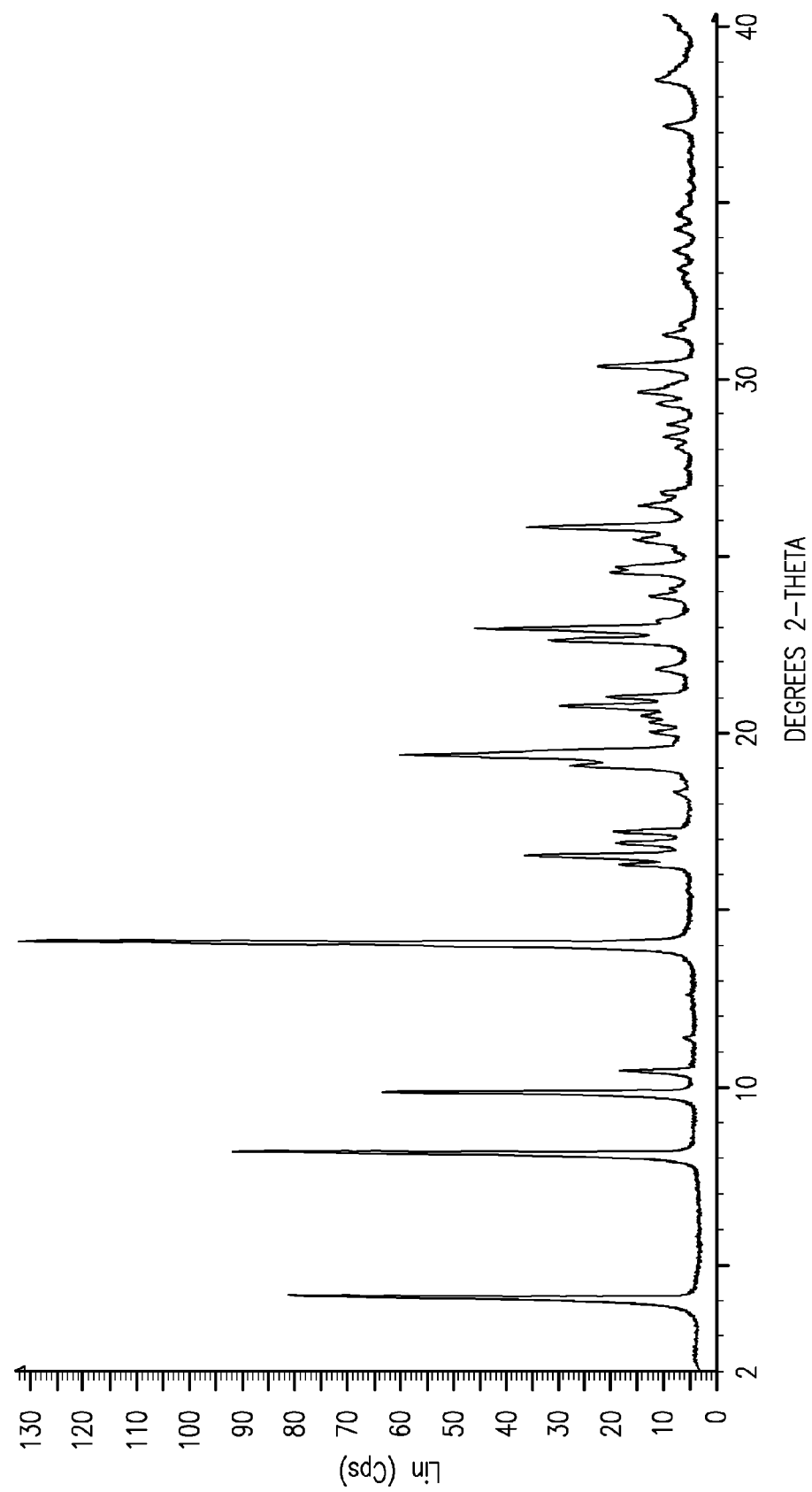
FIG. 1 is an X-ray powder diffraction (XRPD) pattern of crystalline anhydrous (2S,3R,4R,5S,6R)-2-(4-chloro-3-(4-ethoxybenzyl)phenyl)-6-(methylthio)tetrahydro-2H-pyran-3,4,5-triol Form 1. The diffractogram was obtained using a Bruker D8 Advance System (Cu Kα radiation) with a VANTEC-1 detector.

This invention is directed, in part, to solid (e.g., crystalline) forms of anhydrous (2S,3R,4R,5S,6R)-2-(4-chloro-3-(4-ethoxybenzyl)phenyl)-6-(methylthio)tetrahydro-2H-pyran-3,4,5-triol:

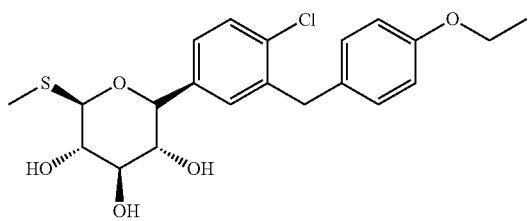

The compound is an inhibitor of the sodium glucose co-transporter 2, and may be useful in the treatment of diabetes and a variety of other diseases and conditions. See U.S. patent application Ser. No. 11/862,690, filed Sep. 28, 2007.

This invention is also directed to dosage forms comprising solid forms of anhydrous (2S,3R,4R,5S,6R)-2-(4-chloro-3-(4-ethoxybenzyl)phenyl)-6-(methylthio)tetrahydro-2H-pyran-3,4,5-triol, and to methods of their use.

5.1. Definitions

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or to prevent its recurrence. A prophylactically effective amount of a compound means an amount of therapeutic agent, alone or in combination with other agents, which provides a prophylactic benefit in the prevention of the disease or condition. The term "prophylactically effective amount" can encompass an amount that improves overall prophylaxis or enhances the prophylactic efficacy of another prophylactic agent.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder or one or more of its symptoms, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should also be noted that any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit. Structures that represent compounds with one or more chiral centers, but which do not indicate stereochemistry (e.g., with bolded or dashed lines), encompasses pure stereoisomers and mixtures (e.g., racemic mixtures) thereof. Similarly, names of compounds having one or more chiral centers that do not specify the stereochemistry of those centers encompass pure stereoisomers and mixtures thereof.

5.2. Solid Forms

This invention is directed to solid forms of anhydrous (2S,3R,4R,5S,6R)-2-(4-chloro-3-(4-ethoxybenzyl)phenyl)-6-(methylthio)tetrahydro-2H-pyran-3,4,5-triol:

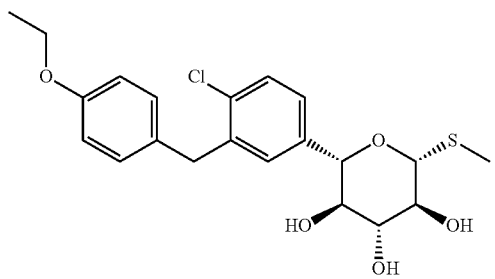 [SMILES: CCOc1ccc(Cc2cc([C@@H]3O[C@H](SC)[C@@H](O)[C@H](O)[C@H]3O)ccc2Cl)cc1]

One embodiment is directed to solid amorphous forms. Another is directed to solid crystalline forms.

A particular crystalline form referred to herein as Form 1 has a differential scanning calorimetry (DSC) endotherm at about 124° C. In this context, the term "about" means±5.0° C.

In one embodiment, the form provides an X-ray powder diffraction (XRPD) pattern that contains peaks at one or more of about 4.0, 8.1, 9.8, 14.0 and/or 19.3 degrees 2θ. In this context, the term "about" means±0.3 degrees. As those skilled in the art are well aware, the relative intensities of peaks in an XRPD pattern can vary depending on how the sample is prepared and how the data is collected. With this in mind, an example of an XRPD pattern of this form is provided in FIG. 1.

Figure 2:
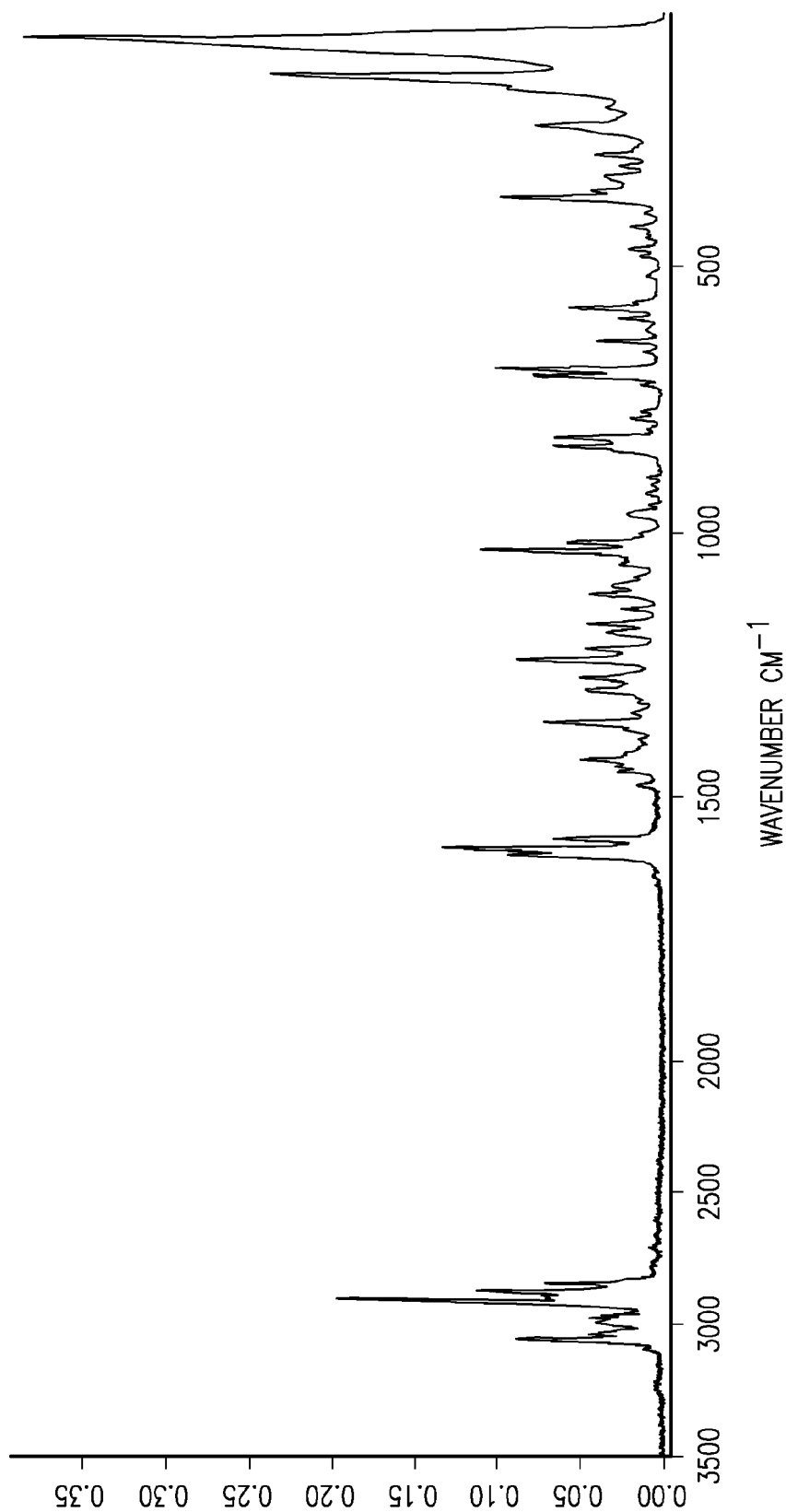
FIG. 2 is a FT-Raman spectrum of crystalline anhydrous (2S,3R,4R,5S,6R)-2-(4-chloro-3-(4-ethoxybenzyl)phenyl)-6-(methylthio)tetrahydro-2H-pyran-3,4,5-triol Form 1. The spectrum was obtained using a Bruker RFS100 with 1064 nm excitation.

In one embodiment, the form provides a Raman spectrum with peaks at one or more of about 3068, 2929, 2888, 2881, 1615, 1603, 1244, 1037, 692 and/or 372 cm$^{-1}$. In this context, the term "about" means±2 cm$^{-1}$. As those skilled in the art are well aware, the relative intensities of peaks in a Raman spectrum can vary depending on how the sample is prepared and how the data is collected. With this in mind, an example of a FT-Raman spectrum of this form is provided in FIG. 2.

Figure 3:
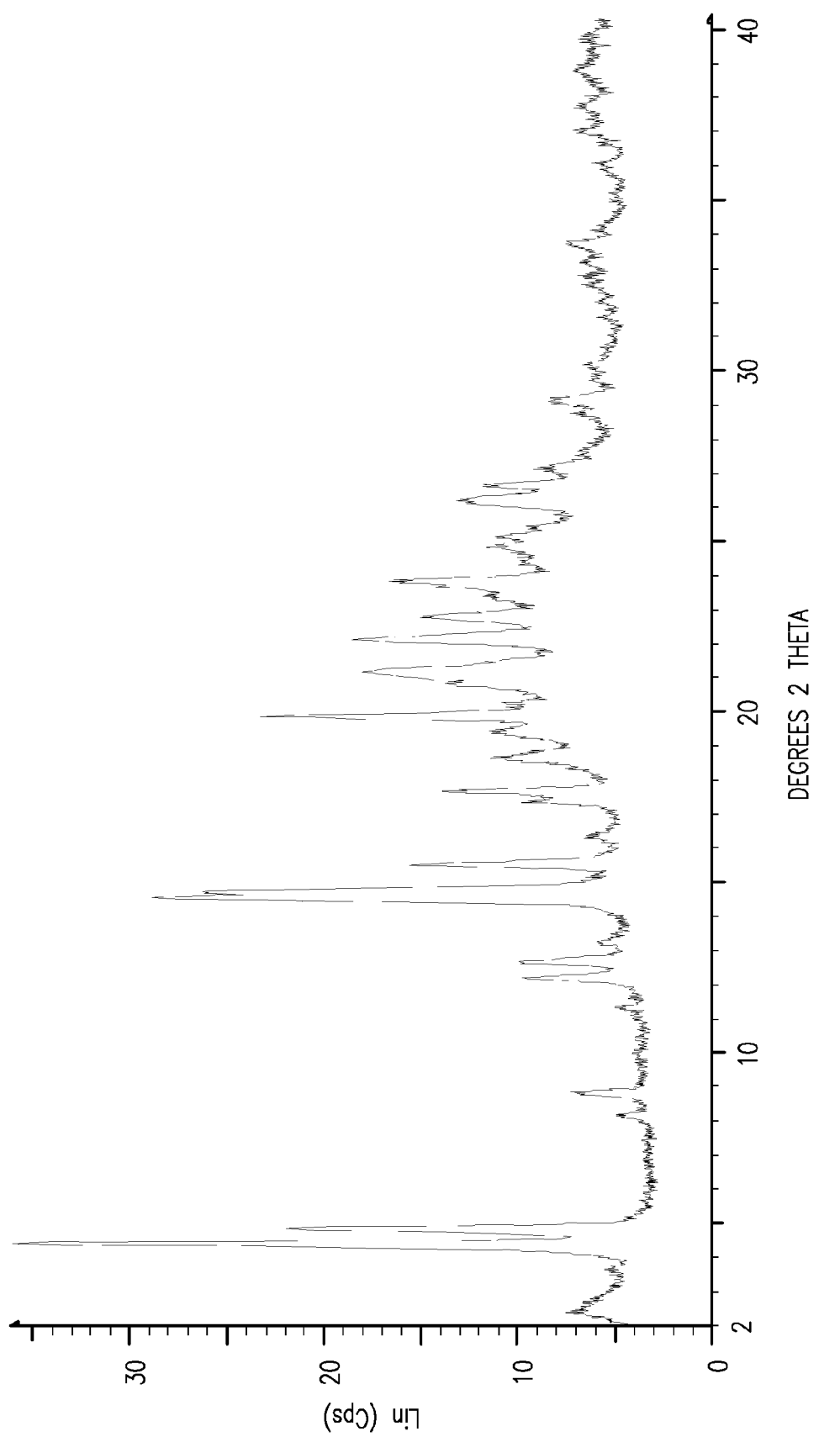
FIG. 3 is an XRPD pattern of crystalline anhydrous (2S,3R,4R,5S,6R)-2-(4-chloro-3-(4-ethoxybenzyl)phenyl)-6-(methylthio)tetrahydro-2H-pyran-3,4,5-triol Form 2. The diffractogram was obtained using a Bruker D8 Advance System (Cu Kα radiation) with a VANTEC-1 detector.

A particular crystalline form referred to herein as Form 2 has a differential scanning calorimetry (DSC) endotherm at about 134° C. In this context, the term "about" means±5.0° C. In one embodiment, the form provides an XRPD pattern that contains peaks at one or more of about 4.4, 4.8, 14.5, 14.7, 15.5, 21.2, 22.1 and/or 23.8 degrees 2θ. In this context, the term "about" means±0.3 degrees. An example of an XRPD pattern of this form is provided in FIG. 3.

Figure 4:
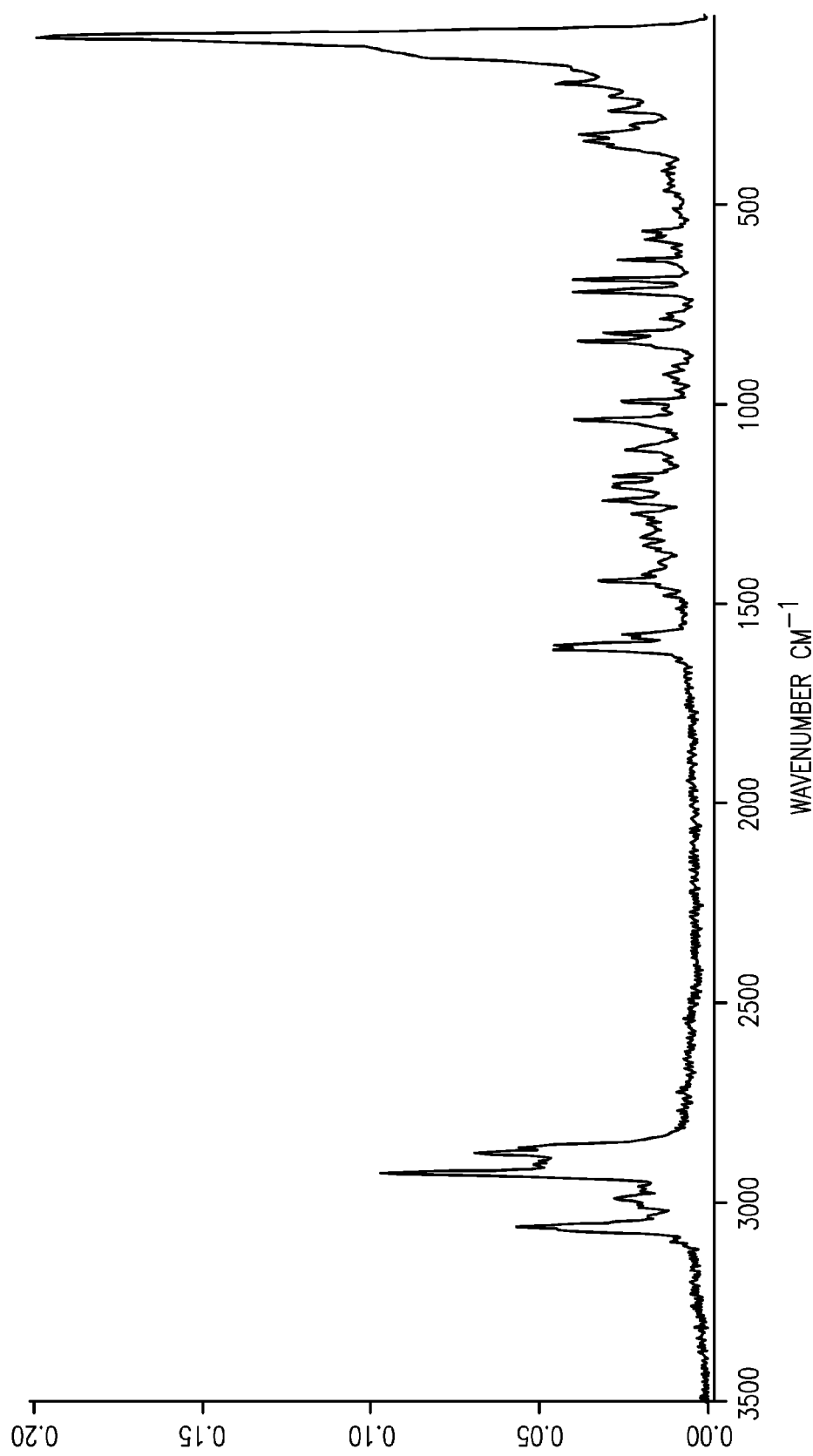
FIG. 4 is a FT-Raman spectrum of crystalline anhydrous (2S,3R,4R,5S,6R)-2-(4-chloro-3-(4-ethoxybenzyl)phenyl)-6-(methylthio)tetrahydro-2H-pyran-3,4,5-triol Form 2. The spectrum was obtained using a Bruker RFS100 with 1064 nm excitation.

In one embodiment, the form provides a Raman spectrum with peaks at one or more of about 3061, 2927, 2877, 2864, 1605, 1038, 842 and/or 719 cm$^{-1}$. In this context, the term "about" means±2 cm$^{-1}$. An example of a FT-Raman spectrum of this form is provided in FIG. 4.

This invention encompasses compositions comprising different crystalline forms of anhydrous (2S,3R,4R,5S,6R)-2-(4-chloro-3-(4-ethoxybenzyl)phenyl)-6-(methylthio)tetrahydro-2H-pyran-3,4,5-triol. The invention also encompasses solids that are mixtures of both amorphous and crystalline forms of the compound. Certain such solids comprise crystalline (2S,3R,4R,5S,6R)-2-(4-chloro-3-(4-ethoxybenzyl)phenyl)-6-(methylthio)tetrahydro-2H-pyran-3,4,5-triol in an amount of at least about 50, 75, 80, 85, 90, 95 or 99 weight percent.

5.3. Methods of Use

This invention encompasses a method of inhibiting SGLT2 activity, which comprises contacting SGLT2 with an effective amount of a compound of the invention (i.e., a compound disclosed herein). In one embodiment, the protein is in vivo. In another, it is ex vivo.

The invention also encompasses a method of decreasing blood glucose in a patient (e.g., a mammal, such as a human, dog or cat), which comprises administering to the patient an effective amount of a compound of the invention.

The invention also encompasses a method of increasing the excretion of glucose in the urine of a patient, which comprises administering to the patient an effective amount of a compound of the invention.

The invention also encompasses a method of restoring or increasing insulin sensitivity in a patient, which comprises administering to the patient an effective amount of a compound of the invention.

The invention also encompasses a method of treating, managing or preventing a disease or disorder in a patient, which comprises administering to the patient a therapeutically or prophylactically effective amount of a compound of the invention. Examples of diseases and disorders include atherosclerosis, cardiovascular disease, diabetes (Type 1 and 2), hyperglycaemia, hypertension, lipid disorders, obesity, and Syndrome X. A particular disease is type 2 diabetes.

The amount, route of administration and dosing schedule of a compound may depend upon factors such as the specific indication to be treated, prevented or managed, and the age, gender and condition of the patient. The roles played by such factors are well known in the art, and may be accommodated by routine experimentation.

5.4. Pharmaceutical Formulations

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

5.4.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., Remington's Pharmaceutical Sciences, 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.4.2. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5.4.3. Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or hydrates of the active ingredients can be used to further adjust the properties of the resulting composition.

6. EXAMPLES

Aspects of this invention can be understood from the following examples.

6.1. Synthesis of ((3aS,5R,6S,6aS)-6-hydroxy-2,2-dimethyltetrahydrofuro[2,3-d][1,3]dioxol-5-yl)(morpholino)methanone To a 12 L three-necked round bottom flask with mechanical stirrer, rubber septum with temperature probe and gas bubbler was charged L-(−)-xylose (504.40 g, 3.360 mol), acetone (5 L, reagent grade) and anhydrous $MgSO_4$ powder (811.23 g, 6.740 mol/2.0 equiv). The suspension was set stirring at ambient and then concentrated $H_2SO_4$ (50 mL, 0.938 mol/0.28 equiv) was added. A slow mild exotherm was noticed (temperature rose to 24° C. over about 1 hr) and the reaction was allowed to stir at ambient overnight. After 16.25 hours, TLC suggested all L-xylose had been consumed, with the major product being the bis-acetonide along with some (3aS,5S,6R,6aS)-5-(hydroxymethyl)-2,2-dimethyltetrahydrofuro[2,3-d][1,3]dioxol-6-ol. The reaction mixture was filtered and the collected solids were washed twice with acetone (500 mL per wash). The stirring yellow filtrate was neutralized with concentrated $NH_4OH$ solution (39 mL) to pH=8.7. After stirring for 10 min, the suspended solids were removed by filtration. The filtrate was concentrated to afford crude bis-acetonide intermediate as a yellow oil (725.23 g). The yellow oil was suspended in 2.5 L water stirring in a 5 L three-necked round bottom flask with mechanical stirrer, rubber septum with temperature probe and gas bubbler. The pH was adjusted from 9 to 2 with 1N aq. HCl (142 mL) and stirred at room temperature for 6 h until GC showed sufficient conversion of the bis-acetonide intermediate to (3aS,5S,6R,6aS)-5-(hydroxymethyl)-2,2-dimethyltetrahydrofuro[2,3-d][1,3]dioxol-6-ol. The reaction was neutralized by the addition of 50% w/w aq. $K_2HPO_4$ until pH=7. The solvent was then evaporated and ethyl acetate (1.25 L) was added to give a white suspension which was filtered. The filtrate was concentrated in vacuo to afford an orange oil which was dissolved in 1 L methyl tert-butyl ether. This solution had KF 0.23 wt % water and was concentrated to afford (3aS,5S,6R,6aS)-5-(hydroxymethyl)-2,2-dimethyltetrahydrofuro[2,3-d][1,3]dioxol-6-ol as an orange oil (551.23 g, 86% yield, 96.7 area % pure by GC). $^1H$ NMR (400 MHz, DMSO-$d_6$) δ 1.22 (s, 3H) 1.37 (s, 3H) 3.51 (dd, J=11.12, 5.81 Hz, 1H) 3.61 (dd, J=11.12, 5.05 Hz, 1H) 3.93-4.00 (m, 1H) 3.96 (s, 1H) 4.36 (d, J=3.79 Hz, 1H) 4.86 (br. s., 2H) 5.79 (d, J=3.54 Hz, 1H). $^{13}C$ NMR (101 MHz, DMSO-$d_6$) δ 26.48, 27.02, 59.30, 73.88, 81.71, 85.48, 104.69, 110.73.

To a solution of (3aS,5S,6R,6aS)-5-(hydroxymethyl)-2,2-dimethyltetrahydrofuro[2,3-d][1,3]dioxol-6-ol (25.0 g, 131 mmol) in acetone (375 mL, 15×) and $H_2O$ (125 mL, 5×) was added $NaHCO_3$ (33.0 g, 3.0 equiv), NaBr (2.8 g, 20 mol %) and TEMPO (0.40 g, 2 mol %) at 20° C. The mixture was cooled to 0-5° C. and solid trichloroisocyanuric acid (TCCA, 30.5 g, 1.0 equiv) was then added in portions. The suspension was stirred at 20° C. for 24 h. Methanol (20 mL) was added and the mixture was stirred at 20° C. for 1 h. A white suspension was formed at this point. The mixture was filtered, washed with acetone (50 mL, 2×). The organic solvent was removed under vacuum and the aqueous layer was extracted with EtOAc (300 mL, 12× ×3) and the combined organic layers were concentrated to afford an oily mixture with some solid residue. Acetone (125 mL, 5×) was added and the mixture was filtered. The acetone solution was then concentrated to afford the desired acid ((3aS,5R,6S,6aS)-6-hydroxy-2,2-dimethyltetrahydrofuro[2,3-d][1,3]dioxole-5-carboxylic acid) as a yellow solid (21.0 g, 79%). $^1H$ NMR (methanol-$d_4$), δ 6.00 (d, J=3.2 Hz, 1H), 4.72 d, J=3.2 Hz, 1H), 4.53 (d, J=3.2 Hz, 1H), 4.38 (d, J=3.2 Hz, 1H), 1.44 (s, 3H), 1.32 (s, 3H).

To a solution of (3aS,5R,6S,6aS)-6-hydroxy-2,2-dimethyltetrahydrofuro[2,3-d][1,3]dioxole-5-carboxylic acid (5.0 g, 24.5 mmol) in THF (100 mL, 20×) was added TBTU (11.8 g, 1.5 equiv), N-methylmorpholine (NMM, 4.1 mL, 1.5 equiv) and the mixture was stirred at 20° C. for 30 min. Morpholine (3.2 mL, 1.5 equiv) was then added, and the reaction mixture was stirred at 20° C. for an additional 6 h. The solid was filtered off by filtration and the cake was washed with THF (10 mL, 2× ×2). The organic solution was concentrated under vacuum and the residue was purified by silica gel column chromatography (hexanes:EtOAc, from 1:4 to 4:1) to afford 4.3 g of the desired morpholine amide (64%) as a white solid. $^1H$ NMR (CDCl$_3$), δ 6.02 (d, J=3.2 Hz, 1H), 5.11 (br s, 1H), 4.62 (d, J=3.2 Hz, 1H), 4.58 (d, J=3.2 Hz, 1H), 3.9-3.5 (m, 8H), 1.51 (s, 3H), 1.35 (s, 3H).

6.2. Alternative synthesis of ((3aS,5R,6S,6aS)-6-hydroxy-2,2-dimethyltetrahydrofuro[2,3-d][1,3]dioxol-5-yl)(morpholino)methanone A solution of the diol (3aS,5S,6R,6aS)-5-(hydroxymethyl)-2,2-dimethyltetrahydrofuro[2,3-d][1,3]dioxol-6-ol in acetonitrile (5.38 kg, 65% w/w, 3.50 kg active, 18.40 mol), acetonitrile (10.5 L) and TEMPO (28.4 g, 1 mol %) were added to a solution of $K_2HPO_4$ (0.32 kg, 1.84 mol) and $KH_2PO_4$ (1.25 kg, 9.20 mol) in water (10.5 L). A solution of $NaClO_2$ (3.12 kg, 80% w/w, 27.6 mole, 1.50 eq) in water (7.0 L) and a solution of $K_2HPO_4$ (2.89 kg, 0.90 eq) in water (3.0 L) were prepared with cooling. Bleach (3.0 L, approximate 6% household grade) was mixed with the $K_2HPO_4$ solution. Approximately 20% of the $NaClO_2$ solution (1.6 L) and bleach/$K_2HPO_4$ solution (400 mL, ~1 mol %) were added. The remainders of the two solutions were added simultaneously. The reaction mixture turned dark red brown and slow exotherm was observed. The addition rate of the $NaClO_2$ solution was about 40 mL/min (3-4 h addition) and the addition rate for the bleach/$K_2HPO_4$ solution was about 10-12 mL/min (10 hr addition) while maintaining the batch at 15-25° C. Additional charges of TEMPO (14.3 g, 0.5 mol %) were performed every 5-6 hr until the reaction went to completion (usually two charges are sufficient). Nitrogen sweep of the headspace to a scrubber with aqueous was performed to keep the green-yellowish gas from accumulating in the vessel. The reaction mixture was cooled to <10° C. and quenched with Na$_2$SO$_3$ (1.4 kg, 0.6 eq) in three portions over 1 hr. The reaction mixture was then acidified with H$_3$PO$_4$ until pH reached 2.0-2.1 (2.5-2.7 L) at 5-15° C. The layers were separated and the aqueous layer was extracted with acetonitrile (10.5 L×3). The combined organic layer was concentrated under vacuo (~100-120 torr) at <35° C. (28-32° C. vapor, 45-50° C. bath) to low volume (~6-7 L) and then flushed with acetonitrile (40 L) until KF of the solution reached <1% when diluted to volume of about 12-15 L with acetonitrile. Morpholine (1.61 L, 18.4 mol, 1.0 eq) was added over 4-6 h and the slurry was aged overnight under nitrogen. The mixture was cooled to 0-5° C. and aged for 3 hours then filtered. The filter cake was washed with acetonitrile (10 L). Drying under flowing nitrogen gave 4.13 kg of the morpholine salt of ((3aS,5R,6S,6aS)-6-hydroxy-2,2-dimethyltetrahydrofuro[2,3-d][1,3]dioxole-5-carboxylic acid as a white solid (92-94% pure based on $^1$H NMR with 1,4-dimethoxybenzene as the internal standard), 72-75% yield corrected for purity. $^1$H NMR (D$_2$O) δ 5.96 (d, J=3.6 Hz, 1H), 4.58 (d, J=3.6 Hz, 1H), 4.53 (d, J=3.2 Hz, 1H), 4.30 (d, J=3.2 Hz, 1H), 3.84 (m, 2H), 3.18 (m, 2H), 1.40 (s, 1H), 1.25 (s, 1H). $^{13}$H NMR (D$_2$O) δ 174.5, 112.5, 104.6, 84.2, 81.7, 75.0, 63.6, 43.1, 25.6, 25.1.

The morpholine salt of ((3aS,5R,6S,6aS)-6-hydroxy-2,2-dimethyltetrahydrofuro[2,3-d][1,3]dioxole-5-carboxylic acid (7.85 kg, 26.9 mol), morpholine (2.40 L, 27.5 mol) and boric acid (340 g, 5.49 mol, 0.2 eq) were added to toluene (31 L). The resulting slurry was degassed and heated at reflux with a Dean-Stark trap under nitrogen for 12 h and then cooled to room temperature. The mixture was filtered to remove insolubles and the filter cake washed with toluene (5 L). The filtrate was concentrated to about 14 L and flushed with toluene (~80 L) to remove excess morpholine. When final volume reached ~12 L, heptane (14 L) was added slowly at 60-70° C. The resulting slurry was cooled gradually to room temperature and aged for 3 h. It was then filtered and washed with heptane (12 L) and dry under nitrogen gave a slightly pink solid (6.26 kg, 97% pure, 98% yield). m.p.: 136° C. (DSC). $^1$H NMR (CDCl$_3$), δ 6.02 (d, J=3.2 Hz, 1H), 5.11 (br s, 1H), 4.62 (d, J=3.2 Hz, 1H), 4.58 (d, J=3.2 Hz, 1H), 3.9-3.5 (m, 8H), 1.51 (s, 3H), 1.35 (s, 3H). $^{13}$C NMR (methanol-d$_4$) δ 26.84, 27.61, 44.24, 47.45, 68.16, 77.14, 81.14, 86.80, 106.87, 113.68, 169.05.

6.3. Synthesis of 1-chloro-2-(4-ethoxybenzyl)-4-iodobenzene

A 2 L three-necked round bottom flask with mechanical stirrer, rubber septum with temperature probe and pressure-equalized addition funnel with gas bubbler was charged with 2-chloro-5-iodobenzoic acid (199.41 g, 0.706 mol), dichloromethane (1.2 L, KF=0.003 wt % water) and the suspension was set stirring at ambient temperature. Then N,N-dimethylformamide (0.6 mL, 1.1 mol %) was added followed by oxalyl chloride (63 mL, 0.722 mol, 1.02 equiv) which was added over 11 min. The reaction was allowed to stir at ambient overnight and became a solution. After 18.75 hours, additional oxalyl chloride (6 mL, 0.069 mol, 0.10 equiv) was added to consume unreacted starting material. After 2 hours, the reaction mixture was concentrated in vacuo to afford crude 2-chloro-5-iodobenzoyl chloride as a pale yellow foam which will be carried forward to the next step.

A jacketed 2 L three-necked round bottom flask with mechanical stirrer, rubber septum with temperature probe and pressure-equalized addition funnel with gas bubbler was charged with aluminum chloride (97.68 g, 0.733 mol, 1.04 equiv), dichloromethane (0.65 L, KF=0.003 wt % water) and the suspension was set stirring under nitrogen and was cooled to about 6° C. Then ethoxybenzene (90 mL, 0.712 mol, 1.01 equiv) was added over 7 minutes keeping internal temperature below 9° C. The resulting orange solution was diluted with dichloromethane (75 mL) and was cooled to −7° C. Then a solution of 2-chloro-5-iodobenzoyl chloride (≤0.706 mol) in 350 mL dichloromethane was added over 13 minutes keeping the internal temperature below +3° C. The reaction mixture was warmed slightly and held at +5° C. for 2 hours. HPLC analysis suggested the reaction was complete and the reaction was quenched into 450 mL pre-cooled (−5° C.) 2N aq. HCl with stirring in a jacketed round bottom flask. This quench was done in portions over 10 min with internal temperature remaining below 28° C. The quenched biphasic mixture was stirred at 20° C. for 45 min and the lower organic phase was washed with 1N aq. HCl (200 mL), twice with saturated aq. sodium bicarbonate (200 mL per wash), and with saturated aq. sodium chloride (200 mL). The washed extract was concentrated on a rotary evaporator to afford crude (2-chloro-5-iodophenyl) (4-ethoxyphenyl)methanone as an off-white solid (268.93 g, 99.0 area % by HPLC at 220 nm, 1.0 area % regioisomer at 200 nm, 98.5% "as-is" yield).

A jacketed 1 L three-necked round bottom flask with mechanical stirrer, rubber septum with temperature probe and gas bubbler was charged with crude (2-chloro-5-iodophenyl) (4-ethoxyphenyl)methanone (30.13 g, 77.93 mmol), acetonitrile (300 mL, KF=0.004 wt % water) and the suspension was set stirring under nitrogen and was cooled to about 5° C. Then triethylsilane (28 mL, 175.30 mmol, 2.25 equiv) was added followed by boron trifluoride-diethyletherate (24 mL, 194.46 mmol, 2.50 equiv) which was added over about 30 seconds. The reaction was warmed to ambient over 30 min and was stirred for 17 hours. The reaction was diluted with methyl tert-butyl ether (150 mL) followed by saturated aq sodium bicarbonate (150 mL) which was added over about 1 minutes. Mild gas evolution was noticed and the biphasic solution was stirred at ambient for 45 minutes. The upper organic phase was washed with saturated aq. sodium bicarbonate (100 mL), and with saturated aq. sodium chloride (50 mL). The washed extract was concentrated on a rotary evaporator to about one half of its original volume and was diluted with water (70 mL). Further concentration in vacuo at 45° C. was done until white prills formed which were allowed to cool to ambient while stirring. After about 30 minutes at ambient, the suspended solids were isolated by filtration, washed with water (30 mL), and were dried in vacuo at 45° C. After about 2.5 hours, this afforded 1-chloro-2-(4-ethoxybenzyl)-4-iodobenzene as a slightly waxy white granular powder (28.28 g, 98.2 area % by HPLC at 220 nm, 97.4% "as-is" yield).

6.4. Synthesis of (4-chloro-3-(4-ethoxybenzyl)phenyl)((3aS,5R,6S,6aS)-6-hydroxy-2,2-dimethyltetrahydrofuro[[2,3-d]1,3]dioxol-5-yl)methanone To a solution of 1-chloro-2-(4-ethoxybenzyl)-4-iodobenzene (500 mg, 1.34 mmol) in THF (5.0 mL) was added i-PrMgCl (2.0M in THF, 1.0 mL, 2.00 mmol) at 0-5° C., and the mixture was stirred for 1.5 h at 0-5° C. A solution of (3aS,5R,6S,6aS)-6-hydroxy-2,2-dimethyltetrahydrofuro[2,3-d][1,3]dioxol-5-yl)(morpholino)methanone (146.5 mg, 0.536 mmol) in THF (1.0 mL) was added dropwise at 0-5° C. and the mixture was kept stirring for 1 h, warmed to 20° C. and stirred at 20° C. for 2 hours. The reaction was quenched with saturated aq NH$_4$Cl, extracted with MTBE, washed with brine. The organic layer was concentrated and the residue was purified by silica gel column chromatography to afford the desired ketone (178 mg, 76%) as a white solid. $^1$H NMR (CDCl$_3$) δ 7.88 (dd, J=8.4, 2.0 Hz, 1H), 7.82 (d, J=2.0 Hz, 1H), 7.50 (d, J=8.4 Hz, 1H), 7.12 (d, J=8.4 Hz, 2H), 6.86 (d, J=8.4 Hz, 2H), 6.07 (d, J=3.2 Hz, 1H), 5.21 (d, J=3.2 Hz, 1H), 4.58 (d, J=3.2 Hz, 1H), 4.56 (d, J=3.2 Hz, 1H), 4.16 (d, J=7.2 Hz, 2H), 4.03 (q, J=7.2 Hz, 2H), 1.54 (s, 3H), 1.42 (t, J=7.2 Hz, 3H), 1.37 (s, 3H).

6.5. Alternative synthesis of (4-chloro-3-(4-ethoxybenzyl)phenyl)((3aS,5R,6S,6aS)-6-hydroxy-2,2-dimethyltetrahydrofuro[2,3-d][1,3]dioxol-5-yl) methanone To a 20 L reactor equipped with a mechanical stirrer, a temperature controller and a nitrogen inlet was charged with the iodide (3.00 kg, 8.05 mol) and THF (8 L, 4× to the morpholinoamide) at room temperature and cooled to –5° C. To the above solution was added dropwise a solution of i-PrMgCl in THF (Aldrich 2 M, 4.39 L, 8.82 mol) at –5° C. over 3 hours. This Grignard solution was used in the ketone formation below.

To a 50 L reactor equipped with a mechanical stirrer, a temperature controller, and a nitrogen inlet was charged the morpholinoamide (HPLC purity=97 wt %, 2.01 kg, 7.34 mol) and THF (11 L, 5.5×) at room temperature and stirred for 45 minutes at room temperature and for 15 minutes at 30° C. The homogeneous solution was then cooled to –25° C. To this solution was added a solution of t-BuMgCl in THF (Aldrich 1 M, 7.32 L, 7.91 mol) at –25° C. over 3 hours. Then the above Grignard solution was added to this solution at –20 over 41 minutes. The resulting solution was further stirred at –20° C. before quench. The reaction mixture was added to 10 wt % aqueous NH$_4$Cl (10 L, 5×) at 0° C. with vigorous stirring, and stirred for 30 minutes at 0° C. To this mixture was added slowly 6 N HCl (4 L, 2×) at 0° C. to obtain a clear solution and stirred for 30 minutes at 10° C. After phase split, the organic layer was washed with 25 wt % aq NaCl (5 L, 2.5×). Then the organic layer was concentrated to a 3× solution under the conditions (200 mbar, bath temp 50° C.). EtOAc (24 L, 12×) was added, and evaporated to a 3× solution under the conditions (150 mbar, bath temp 50° C.). After removed solids by a polish filtration, EtOAc (4 L, 2×) was added and concentrated to dryness (150 mbar, bath temp 50° C.). The wet cake was then transferred to a 50 L reactor equipped with a mechanical stirrer, a temperature controller and a nitrogen inlet. After EtOAc was added, the suspension was heated at 70° C. to obtain a 2.5× homogeneous solution. To the resulting homogeneous solution was added slowly heptane (5 L, 2.5×) at the same temperature. A homogeneous solution was seeded and heptane (15 L, 7.5×) was added slowly to a little cloudy solution at 70° C. After stirred for 0.5 h at 70° C., the suspension was slowly cooled to 60° C. and stirred for 1 h at 60° C. The suspension was then slowly cool to room temperature and stirred for 14 h at the same temperature. The crystals were collected and washed with heptane (8 L, 4×), dried under vacuum at 45° C. to give the desired ketone as fluffy solids (2.57 kg, 100 wt % by HPLC, purity-adjusted yield: 81%).

6.6. Synthesis of (2S,3S,4R,5S,6R)-2-(4-chloro-3-(4-ethoxybenzyl)phenyl)-6-(methylthio)tetrahydro-2H-pyran-3,4,5-triyl triacetate To a solution of the ketone (4-chloro-3-(4-ethoxybenzyl) phenyl)-((3aS,5R,6S,6aS)-6-hydroxy-2,2-dimethyltetrahydrofuro[2,3-d][1,3]dioxol-5-yl)methanone (114.7 g, 0.265 mol) in MeOH (2 L, 17×) was added CeCl$_3$.7H$_2$O (118.5 g, 1.2 equiv) and the mixture was stirred at 20° C. until all solids were dissolved. The mixture was then cooled to –78° C. and NaBH$_4$ (12.03 g, 1.2 equiv) was added in portions so that the temperature of the reaction did not exceed –70° C. The mixture was stirred at –78° C. for 1 hour, slowly warmed to 0° C. and quenched with saturated aq NH$_4$Cl (550 mL, 5×). The mixture was concentrated under vacuum to remove MeOH and then extracted with EtOAc (1.1 L, 10× ×2) and washed with brine (550 mL, 5×). The combined organics were concentrated under vacuum to afford the desired alcohol as a colorless oil (crude, 115 g). To this colorless oil was added AcOH (650 mL) and H$_2$O (450 mL) and the mixture was heated to 100° C. and stirred for 15 hours. The mixture was then cooled to room temperature (20° C.) and concentrated under vacuum to give a yellow oil (crude, ~118 g). To this crude oil was added pyridine (500 mL) and the mixture was cooled to 0° C. Then, Ac$_2$O (195 mL, ~8.0 equiv) was added and the mixture was warmed to 20° C. and stirred at 20° C. for 2 h. The reaction was quenched with H$_2$O (500 mL) and diluted with EtOAc (1000 mL). The organic layer was separated and concentrated under vacuum to remove EtOAc and pyridine. The residue was diluted with EtOAc (1000 mL) and washed with aq NaHSO$_4$ (1N, 500 mL, ×2) and brine (300 mL). The organic layer was concentrated to afford the desired tetraacetate intermediate as a yellow foam (~133 g).

To a solution of tetraacetate (133 g, 0.237 mol assuming pure) and thiourea (36.1, 2.0 equiv) in dioxane (530 mL, 4×) was added trimethylsilyl trifluoromethanesulfonate (TMSOTf) (64.5 mL, 1.5 equiv) and the reaction mixture was heated to 80° C. for 3.5 hours. The mixture was cooled to 20° C. and MeI (37 mL, 2.5 equiv) and N,N-diisopropylethylamine (DiPEA) (207 mL, 5.0 equiv) was added and the mixture was stirred at 20° C. for 3 h. The mixture was then diluted with methyl tertiary-butyl ether (MTBE) (1.3 L, 10×) and washed with H$_2$O (650 mL, 5× ×2). The organic layer was separated and concentrated under vacuum to give a yellow solid. To this yellow solid was added MeOH (650 mL, 5×) and the mixture was reslurried at 60° C. for 2 h and then cooled to 0° C. and stirred at 0° C. for 1 hour. The mixture was filtered and the cake was washed with MeOH (0° C., 70 mL, ×3). The cake was dried under vacuum at 45° C. overnight to afford the desired triacetate (2S,3S,4R,5S,6R)-2-(4-chloro-3-(4-ethoxybenzyl)phenyl)-6-(methylthio)tetrahydro-2H-pyran-3,4,5-triyltriacetate (88 g, 60% over 4 steps) as a pale yellow solid. $^1$H NMR (CDCl$_3$) δ 7.37 (d, J=8.0 Hz, 1H), 7.20 (dd, J=8.0, 2.0 Hz, 1H), 7.07 (m, 2H), 6.85 (m, 2H), 5.32 (t, J=9.6 Hz, 1H), 5.20 (t, J=9.6 Hz, 1H), 5.05 (t, J=9.6 Hz, 1H), 4.51 (d, J=9.6 Hz, 1H), 4.38 (d, J=9.6 Hz, 1 h), 4.04 (m, 2H), 2.17 (s, 3H), 2.11 (s, 3H), 2.02 (s, 3H), 1.73 (s, 3H), 1.42 (t, J=7.2 Hz, 3H).

6.7. Alternative synthesis of (2S,3S,4R,5S,6R)-2-(4-chloro-3-(4-ethmbenzyl)phenyl)-6-(methylthio)tetrahydro-2H-pyran-3,4,5-triyl triacetate To a 50 L reactor under nitrogen atmosphere, 40 L MeOH was charged, followed with the ketone (2.50 kg, 5.78 mol) and CeCl$_3$.7H$_2$O (2.16 kg, 1.0 equiv). Methanol (7.5 L) was added as rinse (totally 47.5 L, 19×). A freshly prepared solution of NaBH$_4$ (87.5 g, 0.4 equiv) in aqueous 1 N NaOH (250 mL) was added slowly (35 min) at 15-25° C. The mixture was then stirred for 15 min. HPLC analysis of the reaction mixture showed approximately 90:10 diastereomeric ratio. The reaction was quenched with 10 wt % aq NH$_4$Cl (2.5 L, 1×) and the mixture was concentrated under vacuum to 5×, diluted with water (10 L, 4×) and MTBE (12.5 L, 5×). The mixture was cooled to 10° C. and 6 N aq HCl was added until the pH of the mixture reached 2.0. Stirring was continued for 10 minutes and the layers were separated. The organic layer was washed with H$_2$O (5 L, 2×). The combined aqueous layer was extracted with MTBE (12.5 L, 5×). The combined organic layers were washed with brine (2.5 L, 1×) and concentrated under vacuum to 3×. MeCN (15 L, 6×) was added. The mixture was concentrated again to 10 L (4×) and any solid residue was removed by a polish filtration. The cake was washed with minimal amount of MeCN.

The organic filtrate was transferred to 50 L reactor, and a pre-prepared 20 mol % aqueous H$_2$SO$_4$ solution (61.8 mL 98% concentrated H$_2$SO$_4$ and 5 L H$_2$O) was added. The mixture was heated to 80° C. for 2 hours and then cooled to 20° C. The reaction was quenched with a solution of saturated aqueous K$_2$CO$_3$ (5 L, 2×) and diluted with MTBE (15 L, 6×). The organic layer was separated, washed with brine (5 L, 2×) and concentrated under vacuum to 5 L (2×). MeCN (12.5 L, 5×) was added and the mixture was concentrated to 7.5 L (3×).

The above MeCN solution of (3S,4R,5R,6S)-6-(4-chloro-3-(4-ethoxybenzyl)phenyl)tetrahydro-2H-pyran-2,3,4,5-tetraol was cooled to 10° C., added with dimethylaminopyridine (17.53 g, 2.5 mol %), followed by slow addition of acetic anhydride (3.23 L, 6.0 equiv) and triethylamine (5 L, 2×, 6.0 equiv) so that the temperature of the mixture was kept below 20° C. The reaction was then warmed to 20° C. and stirred for 1 hour and diluted with MTBE (15 L, 6×). The mixture was slowly quenched with water (7.5 L, 3×). The organic layer was separated and washed with saturated aqueous KHCO$_3$ (5 L, 2×), 1 N NaHSO$_4$ (5 L, 2×), and brine (5 L, 2×) in sequence.

The organic layer was then concentrated under vacuum to 5 L (2×). MeCN (12.5 L, 5×) was added and the solution was concentrated to 7.5 L (3×) (KF=0.08%). Dioxane (12.5 L, 5×) was added and the solution was concentrated to 7.50 L (3×) (KF=0.02%). Any residual solid was removed by a polish filtration and the cake was washed with minimal amount of dioxane (500 mL).

To the above filtrate was added thiourea (880 g, 2.0 equiv) and TMSOTf (1.57 L, 1.5 equiv). The reaction mixture was heated to 80° C. for 3 hours (>97% conversion). The mixture was cooled to 20° C. and methyl iodide (541 mL, 1.5 equiv) and diethylisopropylamine (3.02 L, 3.0 equiv) were added and the mixture was stirred at 20° C. for 18 hours. An extra methyl iodide charge (90 mL, 0.25 equiv) was added and the mixture was stirred at 20° C. for 1 hours. The mixture was then diluted with MTBE (25 L, 10×) and washed with water (12.5 L, 5× ×2). The organic layer was separated and concentrated under vacuum to ~5 L (2×). MeOH (12.5 L, 5×) was added and the mixture was concentrated to 5× to afford a slurry. The mixture was then heated at 60° C. for 1 hour and cooled to 0° C. and stirred at 0° C. for 1 hour. The mixture was filtered and the cake was washed with MeOH (0° C., 2.5 L, 1× ×2, 1.0 L, 0.4×). The cake was dried under vacuum at 45° C. overnight to afford the desired triacetate (1.49 kg, 47% over 4 steps) as a pale yellow/off-white solid.

6.8. Synthesis of (2S,3R,4R,5S,6R)-2-(4-chloro-3-(4-ethoxybenzyl)phenyl)-6-(methylthio)tetrahydro-2H-Dyran-3,4,5-triol To a slurry of (2S,3S,4R,5S,6R)-2-(4-chloro-3-(4-ethoxybenzyl)phenyl)-6-(methylthio)tetrahydro-2H-pyran-3,4,5-triyltriacetate (90.0 g, 0.164 mol) in MeOH (900 mL, 10×) was added NaOMe in MeOH (25 wt %, 18 mL, 0.2×) at 20° C. and the mixture was stirred at 20° C. for 2 hours until all solids disappeared. The mixture was then concentrated to 300 mL, added to H$_2$O (1 L) and stirred for 1 hour. The solid was filtered and washed with H2O (100 mL, ×3) and the cake was dried under vacuum at 45° C. overnight to afford the desired methyl thiolate (67.0 g, 95%). 1H NMR (CDCl$_3$) δ 7.38 (d, J=8.4 Hz, 1H), 7.22 (m, 2H), 7.11 (d, J=8.8 Hz, 2H), 6.83 (d, J=8.8 Hz, 2H), 4.35 (d, J=9.6 Hz, 1H), 4.15 (d, J=9.6 Hz, 1H), 4.10-3.95 (m, 3H), 3.64 (t, J=8.8 Hz, 1H), 3.50 (m, 2H), 3.42 (br s, 1H), 2.95 (br s, 1H), 2.57 (br s, 1H), 2.17 (s, 3H), 1.40 (t, J=7.2 Hz, 3H).

6.9. Preparation of Crystalline Anhydrous (2S,3R,4R,5S,6R)-2-(4-chloro-3-(4-ethoxybenzyl)phenyl)-6-(methylthio)tetrahydro-2H-pyran-3,4,5-triol Form 1

Under slightly positive nitrogen pressure, to a 50 L reactor was charged MeOH (12 L) and the triacetate (1.70 Kg, 3.09 mol). Methanol (5 L) was added as a rinse. The slurry was then added NaOMe in MeOH (25 wt %, 340 mL, 0.2×) in 15 minutes at 20° C. and the mixture was stirred at 20° C. for 2 hours until all solids disappeared. To the mixture was added slowly water (25.5 L, 15×) in 45 minutes with 5 g seeding (DSC 123° C.). Solids crashed out and the mixture was stirred at 20° C. for 1 hour, cooled to 0° C. and stirred for 30 minutes. The solid was filtered and washed with water (1.7 L, 1×, ×2) and the cake was dried under vacuum at 45° C. overnight to afford the title compound (m.p. ~123° C. by DSC peak; 1.28 Kg, 97.7% yield).

6.10. Preparation of Crystalline Anhydrous (2S,3R,4R,5S,6R)-2-(4-chloro-3-(4-ethmbenzyl)phenyl)-6-(methylthio)tetrahydro-2H-pyran-3,4,5-triol Form 2

Under slightly positive nitrogen pressure, to a 50 L reactor was charged MEK (2-butanone, 4 L) and (2S,3R,4R,5S,6R)-2-(4-chloro-3-(4-ethoxybenzyl)phenyl)-6-(methylthio)tetrahydro-2H-pyran-3,4,5-triol Form 1 (1.49 Kg). MEK (3.45 L) was added as a rinse. The mixture was heated to 80° C. and heptane (14.9 L, 10×) was slowly added in 1.5 hours. Solids started to crash out and the mixture was charged heptane (14.9 L, 10×) in 6 h. The mixture was stirred at 80° C. for 15 hours. The mixture was cooled to 20° C. in 3 hours and stirred at 20° C. for 1 hour. The solids were filtered and the cake was washed with MEK/heptane (2.5:7.5, v/v, 1.49 L, 1× ×2), dried under nitrogen for 12 hours and under vacuum at 50° C. for 24 hours to afford the title compound as a white solid (m.p. ~134° C. by DSC peak; 1.48 Kg, 98% recovery).

6.11. Alternative Preparation of Crystalline Anhydrous (2S,3R,4R,5S,6R)-2-(4-chloro-3-(4-ethoxybenzyl)phenyl)-6-(methylthio)tetrahydro-2H-pyran-3,4,5-triol Form 2

To a 250 L reactor was charged the triacetate (10 kg) and methanol (75 kg). Sodium methoxide (1.6 kg, 30% solution) was added with 5 kg methanol rinse. The mixture was stirred at room temperature for at least 2 hours or until the reaction was complete. Charcoal (Darco G-60, 1 kg) was added with 5 kg methanol rinse. This mixture was heated at 40° C. for 1 h, cooled to room temperature, and filtered through celite. The cake was washed with methanol (10 kg). Water (100 kg) was added and the mixture was concentrated under vacuum. MTBE (200 kg) and water (50 kg) were added and phases were split. The organic layer was washed with water (100 kg) and concentrated under vacuum. MEK (100 kg) was added and the same about of solvent was distilled under vacuum. This MEK addition and distillation was repeated to dry the solution. Enough MEK was added to produce a solution of (2S,3R,4R,5S,6R)-2-(4-chloro-3-(4-ethoxybenzyl)phenyl)-6-(methylthio)tetrahydro-2H-pyran-3,4,5-triol in 50 L MEK. This solution was polish filtered and heptane (100 L) was added at about 80° C. Form 2 seeds (0.1 kg) were added followed by slow addition of heptane (100 L) as 80° C. Heating was continued for 8 h more at 80° C., cooled to 20° C. over at least 3 hours, held at this temperature for at least 2 hours, filtered, and washed with MEK/heptane. The cake was dried at 50° C. under vacuum to afford the title compound as a white solid (6.6 kg, 86% yield).

All references (e.g., patents and patent applications) cited above are incorporated herein by reference in their entireties.

What is claimed is:

1. A method of treating diabetes in a patient, which comprises administering to a patient in need thereof a therapeutically effective amount of crystalline anhydrous (2S,3R,4R,5S,6R)-2-(4-chloro-3-(4-ethoxybenzyl)phenyl)-6-(methylthio)tetrahydro-2H-pyran-3,4,5-triol having a DSC endotherm at about 124° C.

2. A method of treating diabetes in a patient, which comprises administering to a patient in need thereof a therapeutically effective amount of crystalline anhydrous (2S,3R,4R,5S,6R)-2-(4-chloro-3-(4-ethoxybenzyl)phenyl)-6-(methylthio)tetrahydro-2H-pyran-3,4,5-triol having an X-ray powder diffraction pattern with peaks at one or more of about 4.0, 8.1, 9.8, 14.0 and/or 19.3 degrees 2θ.

3. The method of claim 2, wherein the X-ray powder diffraction pattern contains a peak at about 14.0 degrees 2θ.

4. The method of claim 2, wherein the X-ray powder diffraction pattern is substantially the same as that shown in FIG. 1.

5. The method of claim 1, wherein the crystalline anhydrous (2S,3R,4R,5S,6R)-2-(4-chloro-3-(4-ethoxybenzyl)phenyl)-6-(methylthio)tetrahydro-2H-pyran-3,4,5-triol has a Raman spectrum with peaks at one or more of about 3068, 2929, 2888, 2881, 1615, 1603, 1244, 1037, 692 and/or 372 cm$^{-1}$.

6. The method of claim 5, wherein the Raman spectrum is substantially the same as that shown in FIG. 2.

7. A method of treating diabetes in a patient, which comprises administering to a patient in need thereof a therapeutically effective amount of crystalline anhydrous (2S,3R,4R,5S,6R)-2-(4-chloro-3-(4-ethoxybenzyl)phenyl)-6-(methylthio)tetrahydro-2H-pyran-3,4,5-triol having a DSC endotherm at about 134° C.

8. A method of treating diabetes in a patient, which comprises administering to a patient in need thereof a therapeutically effective amount of crystalline anhydrous (2S,3R,4R,5S,6R)-2-(4-chloro-3-(4-ethoxybenzyl)phenyl)-6-(methylthio)tetrahydro-2H-pyran-3,4,5-triol having an X-ray powder diffraction pattern with peaks at one or more of about 4.4, 4.8, 14.5, 14.7, 15.5, 21.2, 22.1 and/or 23.8 degrees 2θ.

9. The method of claim 8, wherein the X-ray powder diffraction pattern has a peak at about 4.4 degrees 2θ.

10. The method of claim 8, wherein the X-ray powder diffraction pattern is substantially the same as that shown in FIG. 3.

11. The method of claim 7, wherein the crystalline anhydrous (2S,3R,4R,5S,6R)-2-(4-chloro-3-(4-ethoxybenzyl)phenyl)-6-(methylthio)tetrahydro-2H-pyran-3,4,5-triol has a Raman spectrum with peaks at one or more of about 3061, 2927, 2877, 2864, 1605, 1038, 842 and/or 719 cm$^{-1}$.

12. The method of claim 11, wherein the Raman spectrum is substantially the same as that shown in FIG. 4.

13. The method of claim 1, wherein the diabetes is Type 1 diabetes.

14. The method of claim 2, wherein the diabetes is Type 1 diabetes.

15. The method of claim 7, wherein the diabetes is Type 1 diabetes.

16. The method of claim 8, wherein the diabetes is Type 1 diabetes.

* * * * *